United States Patent
Nilsen et al.

(10) Patent No.: US 9,061,977 B2
(45) Date of Patent: Jun. 23, 2015

(54) PURIFICATION OF PRECURSOR COMPOUND BY CRYSTALLISATION

(75) Inventors: Anne Nilsen, Olso (NO); Sondre Nilsen, Oslo (NO)

(73) Assignee: GE Healthcare Limited, Buckinghamshire (GB)

(*) Notice: Subject to any disclaimer, the term of this patent is extended or adjusted under 35 U.S.C. 154(b) by 18 days.

(21) Appl. No.: 13/994,827

(22) PCT Filed: Dec. 19, 2011

(86) PCT No.: PCT/EP2011/073247
§ 371 (c)(1),
(2), (4) Date: Jun. 17, 2013

(87) PCT Pub. No.: WO2012/084831
PCT Pub. Date: Jun. 28, 2012

(65) Prior Publication Data
US 2013/0267730 A1    Oct. 10, 2013

Related U.S. Application Data

(60) Provisional application No. 61/424,695, filed on Dec. 20, 2010.

(30) Foreign Application Priority Data
Dec. 20, 2010   (GB) .................................. 1021530.9

(51) Int. Cl.
| C07C 303/28 | (2006.01) |
| A61K 51/04 | (2006.01) |
| C07B 59/00 | (2006.01) |
| C07C 269/06 | (2006.01) |
| C07C 269/08 | (2006.01) |

(52) U.S. Cl.
CPC ........... *C07C 303/28* (2013.01); *A61K 51/0402* (2013.01); *C07B 59/001* (2013.01); *C07C 269/06* (2013.01); *C07C 269/08* (2013.01); *C07C 2101/04* (2013.01)

(58) Field of Classification Search
None
See application file for complete search history.

(56) References Cited

U.S. PATENT DOCUMENTS

2010/0016626 A1    1/2010   Toyama et al.

FOREIGN PATENT DOCUMENTS

| EP | 1978015 | 10/2008 |
| EP | 2230229 | 9/2010 |

OTHER PUBLICATIONS

Klyza et al. Nuclear Medicine and Biology, 2008, 35, 255-260.*
Wang, et.al. Heteroathom Chemistry, VCH Publishers, Derfield Beack FL, vol. 13, No. 1 Jan. 1, 2002 pp. 77-83.
PCT3P2011/073247 ISRWO Dated Feb. 23, 2012.
GB11021530.9 Search Report Dated Mar. 24, 2011.

* cited by examiner

*Primary Examiner* — Yevegeny Valenrod
(74) *Attorney, Agent, or Firm* — Parks Wood LLC

(57) ABSTRACT

The invention relates to a process for preparation of radiopharmaceutical precursors, and in particular protected amino acid derivatives which are used as precursors for production of radiolabelled amino acids for use in vivo imaging procedures such as positron emission tomography (PET). Particularly, the invention relates to a process for preparation of a precursor useful in the preparation of the [$^{18}$F]-1-amino-3-fluorocyclobutanecarboxylic acid ([$^{18}$F] FACBC) PET tracer.

19 Claims, No Drawings

PURIFICATION OF PRECURSOR COMPOUND BY CRYSTALLISATION

This application is a filing under 35 U.S.C. 371 of international application number PCT/EP2011/073247, filed, which claims priority to Great Britain application number 1021530.9 filed Dec. 20, 2010 and to U.S. application No. 61/424,695 filed Dec. 20, 2010, in the entire disclosure of which is hereby incorporated by reference.

TECHNICAL FIELD OF THE INVENTION

The present invention relates to a method to obtain radiopharmaceutical precursors, and in particular to protected amino acid derivatives which are used as precursors for production of radiolabelled amino acids for use in positron emission tomography (PET). The invention further includes a method to obtain said radiolabelled amino acids.

DESCRIPTION OF RELATED ART

In recent years, a series of radioactive halogen-labelled amino acid compounds including [$^{18}$F]1-amino-3-fluorocyclobutanecarboxylic acid ([$^{18}$F]-FACBC) have been designed as novel radiopharmaceuticals. [$^{18}$F]-FACBC is considered to be effective as a diagnostic agent for highly proliferative tumours, because it has a property of being taken up specifically by amino acid transporters.

EP1978015(A1) provides precursors for the [$^{18}$F]-FACBC compound and methods to obtain said precursors. EP1978015(A1) specifically discloses a method to obtain the precursor syn-1-(N-(t-butoxycarbonyl)amino)-3-[((trifluoromethyl)sulfonyl)oxy]-cyclobutane-1-carboxylic acid ethyl ester wherein said method comprises the following steps:

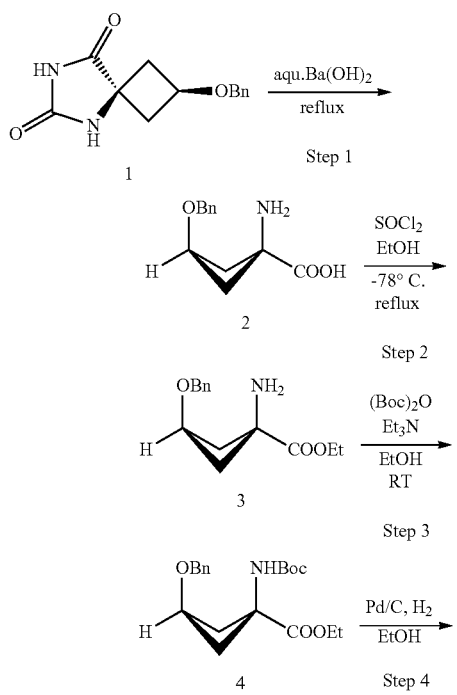

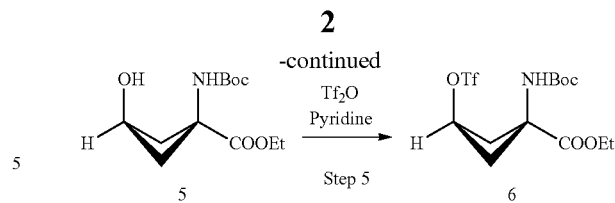

EP1978015(A1) describes that step 1 of the above reaction scheme comprises hydrolysis of syn-5-(3-benzyloxycyclobutane)hydantoin 1 by addition of barium hydroxide Ba(OH)$_2$ to the solution and refluxing the mixture at 114° C. for 24 hours or longer. In the ethyl esterification step 2, syn-1-amino-3-benzyloxycyclobutane-1-carboxylic acid 2 is dissolved in ethanol (EtOH) and reacted with thionyl chloride (SOCl$_2$) to yield syn-1-amino-3-benzyloxycyclobutane-1-carboxylic acid ethyl ester 3. Step 3 comprises addition of tert-butoxycarbonyl (Boc) to the amine function by reaction of 3 with tert-butyl dicarbonate (Boc)$_2$O, and the resultant material is purified by chromatography to obtain syn-1-(N-(t-butoxycarbonyl)amino)-3-benzyloxy-cyclobutane-1-carboxylic acid ethyl ester 4. The benzyl-protected intermediate 4 is then deprotected in step 4 by dissolving compound 4 in ethanol (EtOH), adding palladium on activated carbon (Pd/C) and applying a small positive H$_2$-pressure over the reaction mixture. The resultant material is purified by chromatography to yield syn-1-(N-(t-butoxycarbonyl)amino)-3-benzyloxy-cyclobutane-1-carboxylic acid ethyl ester 5 for use in step 5, which comprises reaction of 5 with trifluoromethanesulfonic anhydride (Tf$_2$O), followed by chromatographic purification with subsequent re-crystallization of the material in order to obtain syn-1-(N-(t-butoxycarbonyl)amino)-3-[((trifluoromethyl)sulfonyl)oxy]-cyclobutane-1-carboxylic acid ethyl ester 6.

The above-described known process is relatively complex, costly and time-consuming, particularly if applied for large-scale production of the precursor compound. It would be desirable to have a process that is more straightforward to carry out, more cost effective, and more amenable to large scale commercial production.

SUMMARY OF THE INVENTION

The present invention is a method useful in the preparation of precursor compounds for [$^{18}$F]-FACBC and similar compounds that is more amenable to large scale commercial production than previously-known methods. As compared with the known method, the method of the present invention permits production of such compounds on a commercial scale without having to handle large amounts of solvents, and also results in improved yields.

DETAILED DESCRIPTION OF THE INVENTION

In one aspect, the present invention relates to a method to obtain a compound of Formula I:

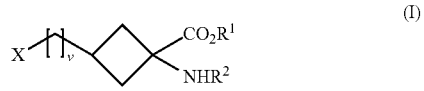

(I)

wherein:
$R^1$ represents a $C_{1-5}$ straight- or branched-chain alkyl group;
$R^2$ represents an amino protecting group;
v is an integer of 0 to 4; and,
X represents a leaving group selected from a halogen, or the group —O—$SO_2$—$R^3$ wherein $R^3$ is a halogen, a straight-chain or branched-chain $C_{1-10}$ alkyl, a straight-chain or branched-chain $C_{1-10}$ haloalkyl, and a $C_{6-10}$ aryl
wherein said method comprises:
(a) debenzylation of a compound of Formula Ia:

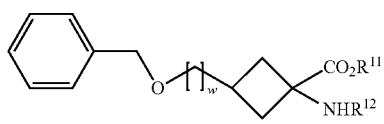

(Ia)

wherein $R^{11}$, $R^{12}$ and w are as defined for $R^1$, $R^2$ and v of Formula I, respectively;
(b) crystallisation of the reaction mixture from step (a) to obtain purified compound of Formula Ib:

(Ib)

wherein $R^{21}$, $R^{22}$ and x are as defined for $R^1$, $R^2$ and v of Formula I, respectively
(c) conversion of purified compound of Formula I obtained in step (b) into a compound of Formula I by reaction with a suitable form of X wherein X is as defined for Formula I.

The term "alkyl" used alone or in combination means a straight-chain or branched-chain group having the general formula $C_nH_{2n+1}$. The value of n in this general formula is specified in particular cases. Examples of some preferred alkyl groups include methyl, ethyl, 1-propyl or isopropyl groups.

By the term "protecting group" is meant a group which inhibits or suppresses undesirable chemical reactions, but which is designed to be sufficiently reactive that it may be cleaved from the functional group in question to obtain the desired product under mild enough conditions that do not modify the rest of the molecule. Protecting groups are well known to those skilled in the art and are described in 'Protective Groups in Organic Synthesis', Theorodora W. Greene and Peter G. M. Wuts, (Fourth Edition, John Wiley & Sons, 2007). Suitable amino protecting groups are well-known in the art. A suitable amino protecting group $R^2$ is a carbamate. Preferably $R^2$ is selected from; tert-butyl carbamate (BOC), 9-fluoroenylmethyl carbamate (Fmoc), methyl carbamate, ethyl carbamate, 2-chloro-3-indenylmethyl carbamate (Climoc), benz[f]inden-3-ylmethyl carbamate (Bimoc), 2,2,2-trichloroethyl carbamate (Troc), 2-chloroethyl carbamate, 1,1-dimethyl-2,2-dibromoethyl carbamate (DB-t-BOC), 1,1-dimethyl-2,2,2-trichloroethyl carbamate (TCBOC), benzyl carbamate (Cbz) and diphenylmethyl carbamate. Most preferably $R^2$ is tert-butyl carbamate, to provide a N-tert-butoxycarbonyl.

The term "leaving group" refers to a moiety suitable for nucleophilic substitution and is a molecular fragment that departs with a pair of electrons in heterolytic bond cleavage.

The term "halogen" or "halo-" used alone or in combination refers to a substituent selected from fluorine, chlorine, bromine or iodine.

The term "$C_{1-10}$ haloalkyl" refers to an alkyl group as defined above comprising between 1-10 carbon atoms wherein at least one hydrogen is replaced with a halogen, wherein halogen is as defined above.

The term "$C_{6-10}$ aryl" refers to a monovalent aromatic hydrocarbon having a single ring (i.e. phenyl) or fused rings (i.e. naphthalene). Unless otherwise defined, such aryl groups typically contain from 6 to 10 carbon ring atoms.

The term "debenzylation" refers to the cleavage of a benzyl substituent from a compound. The term "benzyl" refers to a group with chemical structure $C_6H_5CH_2$—. Debenzylation is a method well-known in the art and is generally carried out by "catalytic hydrogenation", which is a reaction whereby a carbon-carbon bond is cleaved or undergoes "lysis" by hydrogen. Hydrogenolysis is usually carried out catalytically, e.g. using palladium on carbon (Pd/C) as a catalyst. When a catalyst such as Pd/C is used in the debenzylation step, the catalyst is removed from the reaction mixture by filtration prior to the next step. The term "filtration" refers to the mechanical separation of solids from fluids. Non-limiting examples of suitable filtration means for use in the present invention include glass sinter funnel or glass fiber filer in addition to a filter funnel, although other more specialised filter methods are also suitable. Generally, following the debenzylation step (a) and prior to the crystallisation step (b), the reaction solvent is removed by drying. Drying may be carried out by methods well-known to the person skilled in the art e.g. by evaporation under nitrogen flow and/or vacuum drying.

The term "crystallisation" generally refers to the process of formation of solid crystals precipitating from a solution. Crystallisation can be used as a purification method due to the fact that well-formed crystals are expected to be pure because each molecule or ion must fit perfectly into the lattice as it leaves the solution. For crystallisation to occur from a solution it must be supersaturated. This means that the solution has to contain more solute entities dissolved than it would contain under the equilibrium (saturated solution). This can be achieved by various methods, including solvent evaporation, solution cooling, addition of a second solvent to reduce the solubility of the solute (technique known as antisolvent or drown-out), chemical reaction and change in pH. In the method of the invention, a solution of the reactants following step (a) is made. This solution is made using a first solvent in which the reactants easily dissolve.

The term "a suitable form of X" means X as defined herein in a form that can displace the hydroxyl function in a substitution reaction.

Compounds of Formula Ia may be obtained by following or adapting the methods described in EP1978015(A1). For example, compound 4 as specifically described in EP1978015(A1) is a compound of Formula Ia suitable for use in the method of the present invention. The method described in EP1978015(A1) to obtain said compound 4 is illustrated in Scheme 1 below Scheme 1

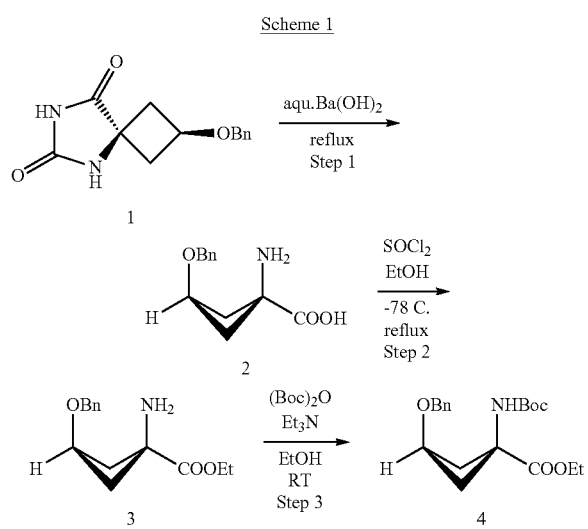

McConathy et al (Appl Rad Isotop 2003; 58: 657-666) also describe methods to obtain compound of Formula Ia. In FIG. 2 of McConathy et al compound 6 is a compound of Formula Ia. The method described by McConathy et al to obtain said compound 6 is illustrated in Scheme 2 below.

Scheme 2

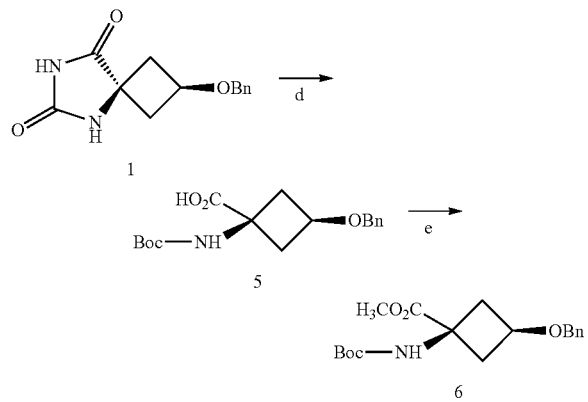

Hydantoin 1 was treated with 3N aqueous sodium hydroxide at 180° C. followed by di-tertbutyl dicarbonate to provide the N-Boc acid 5. Methyl ester 6 was obtained in high yield by reacting 5 with trimethylsilyl diazomethane.

It is within the ordinary skill in the art to adapt the above-described prior art methods to obtain other compounds of Formula Ia that fall within the definition of the present invention. Suitably, the starting hydantoin compound includes a mixture of the syn- and anti-enantiomers. There is no need for actively separating enantiomers, at any stage of the process. Indeed, a slight enrichment of the syn-isomer in the crystalline product has been achieved, as described in Example 2 herein. Such enrichment was observed more pronounced at earlier stages of the crystallization during the introductory experiments. At some lower total yield, the syn/(syn+anti) ratio over 90% was registered. The method of the invention therefore has the further advantage that it can separate the isomers.

Preferably, $R^1$ is methyl or ethyl and is most preferably ethyl. This preferred definition of $R^1$ equally applies to $R^{11}$ and $R^{21}$.

$R^2$ is preferably a carbonate ester protecting group wherein the term "carbonate ester" refers to a functional group consisting of a carbonyl group flanked by two alkoxy groups having general structure $R^xO(C=O)OR^y$. $R^1$ is most preferably a t-butoxycarbonyl group. This preferred definition of $R^2$ equally applies to $R^{12}$ and $R^{22}$.

Preferably, v is 0 or 1 and is most preferably 0. This preferred definition of v equally applies to w and x.

A particularly preferred compound of Formula I is:

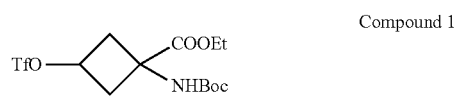

Compound 1

A particularly preferred compound of Formula Ia is:

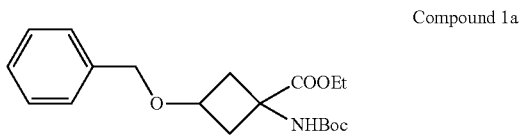 [SMILES: CCOC(=O)C1(NC(=O)OC(C)(C)C)CC(OCc2ccccc2)C1]

Compound 1a

A particularly preferred compound of Formula Ib is:

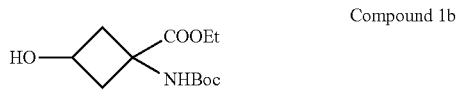

Compound 1b

For the above Compounds 1, 1a and 1b, Et stands for ethyl, OTf for trifluoromethanesulfonic acid and Boc for tert-Butyloxycarbonyl.

The method of the present invention shortens process time and reduces cost of goods in comparison to the prior art methods. In particular for the production of commercial-scale batches of compounds of Formula I, the prior art method using a flash chromatography step to purify the compound of Formula Ib would require a large silica column and large amounts of solvent. By using crystallisation instead of flash chromatography the use of large amounts of solvents is avoided, which provides a benefit both in terms of cost and operator safety.

In a preferred embodiment, X is the group $—O—SO_2—R^3$. Most preferably when X is $—O—SO_2—R^3$, X is selected from the group consisting of toluenesulfonic acid, nitrobenzenesulfonic acid, benzenesulfonic acid, trifluoromethanesulfonic acid, fluorosulfonic acid, and perfluoroalkylsulfonic acid. In an especially preferred embodiment $—O—SO_2—R^3$ is trifluoromethanesulfonic acid. The group $—O—SO_2—R^3$ can be added in step (c) of the method of the invention by reaction of the compound of Formula I with an electrophilic derivative of the desired $—O—SO_2—R^3$ group, which is an example of a "suitable form of X". For example, where it is desired to add trifluoromethanesulfonic acid, the compound of Formula Ib can be reacted with trifluoromethanesulfonic anhydride.

In an alternative preferred embodiment, X is halogen. When X is halogen it is most preferably bromo or chloro. Step (c) wherein X is a halogen may be carried out by methods well known to those skilled in the art. For example, a compound of Formula Ib wherein X is chloro can be obtained by reaction of the compound of Formula I with a chloride-containing reagent such as thionyl chloride, phosphorous pentachloride (PCl$_5$), phosphorous trichloride (PCl$_5$), each of which are examples of a "suitable form of X". A compound of Formula Ib wherein X is bromo can be obtained by reaction of a compound of Formula I with a bromine-containing reagent such as hydrobromic acid (HBr) or phosphorous tribromide (PBr$_3$), again, each of which are examples of a "suitable form of X".

The compound of Formula I is a useful precursor compound in the radiosynthesis of certain $^{18}$F-labelled compounds. Therefore, the present invention also provides a radiosynthetic method to obtain a compound of Formula II:

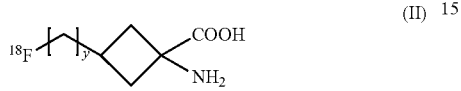
(II)

wherein y is as defined for v of Formula I, wherein said method comprises;
(i) providing a compound of Formula I according to the method as defined herein;
(ii) reaction of said compound of Formula I with a suitable source of $^{18}$F-fluoride to obtain a compound of Formula IIa:

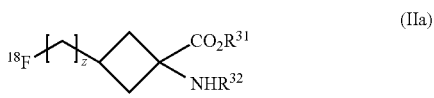
(IIa)

wherein $R^{31}$, $R^{32}$ and z are as defined for $R^1$, $R^2$ and v of Formula I, respectively; and,
(iii) deprotection of the compound of Formula IIa obtained in step (ii) to remove $R^{31}$ and $R^{32}$.

[$^{18}$F]-Fluoride ion is typically obtained as an aqueous solution which is a product of the irradiation of an [$^{18}$O]-water target. Commonly, certain steps are carried out in order to convert [$^{18}$F]-fluoride into a reactive nucleophilic reagent, before its use in nucleophilic radiolabelling reactions. As with non-radioactive fluoridations, these steps include the elimination of water from [$^{18}$F]-fluoride ion and the provision of a suitable counterion (Handbook of Radiopharmaceuticals 2003 Welch & Redvanly eds. Chapter 6 pp 195-227). The radiofluorination reaction is then carried out using anhydrous solvents (Aigbirhio et al 1995 J Fluor Chem; 70: pp 279-87).

To improve the reactivity of [$^{18}$F]-fluoride ion for fluoridation reactions a cationic counterion is added prior to the removal of water. The counterion should possess sufficient solubility within the anhydrous reaction solvent to maintain the solubility of the [$^{18}$F]-fluoride ion. Therefore, counterions that have been used include large but soft metal ions such as rubidium or caesium, potassium complexed with a cryptand such as Kryptofix™, or tetraalkylammonium salts. A preferred counterion for fluoridation reactions is potassium complexed with a cryptand such as Kryptofix™ because of its good solubility in anhydrous solvents and enhanced fluoride reactivity.

Deprotection step (iii) is carried out by methods that are well-known to those of skill in the art. A wide range of protecting groups as well as methods for their removal are described in 'Protective Groups in Organic Synthesis', Theorodora W. Greene and Peter G. M. Wuts, (Fourth Edition, John Wiley & Sons, 2007). In a preferred embodiment, the carboxy protecting group $R^{31}$ is removed prior to the amino protecting group $R^{32}$. For example, where $R^{31}$ is Et it may be removed by basic hydrolysis and where $R^{32}$ is Boc it may be subsequently removed by acidic hydrolysis.

The range of suitable and preferred definitions of v as provided above for Formula I equally apply to y and z of Formulae II and IIa, respectively.

The range of suitable and preferred definitions of $R^1$ and $R^2$ as provided above for Formula I equally apply to $R^{31}$ and $R^{32}$, respectively of Formulae II and IIa.

In a preferred embodiment said compound of Formula II is:

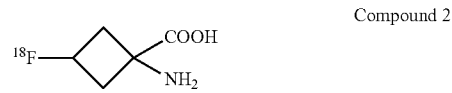
Compound 2 and said compound of Formula IIa is:

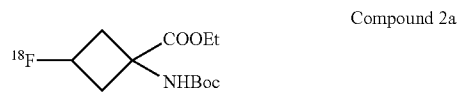
Compound 2a wherein Et is ethyl and Boc is tert-Butyloxycarbonyl.

In a preferred embodiment, steps (ii) and (iii) are carried out on an automated synthesiser. [$^{18}$F]-radiotracers are now often conveniently prepared on an automated radiosynthesis apparatus. There are several commercially-available examples of such apparatus, including Tracerlab™ and Fastlab™ (both from GE Healthcare Ltd). Such apparatus commonly comprises a "cassette", often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps.

A typical cassette for automated synthesis of a compound of Formula II includes:
(i) a vessel containing a compound of Formula I as defined herein; and
(ii) means for eluting the vessel with a suitable source of [$^{18}$F]-fluoride as defined herein.
(iii) an ion-exchange cartridge for removal of excess [$^{18}$F]-fluoride; and,
(iv) a cartridge for deprotection of the compound of Formula IIa to form the compound of Formula II.

The invention will now be described by means of the following experimental examples:

BRIEF DESCRIPTION OF THE EXAMPLES

Example 1 is a comparative example describing a prior art method to obtain a compound of Formula I.

Example 2 describes a method to obtain a compound of Formula I by means of the present invention.

LIST OF ABBREVIATIONS USED IN THE EXAMPLES aq aqueous
TLC thin layer chromatography
hr hour(s)
mmol millimole(s)

ml milliliter(s)
g gram(s)
w/w weight for weight
Et$_2$O diethyl ether
min minute(s)
sat. saturated

EXAMPLES

Example 1

Prior Art Method to Obtain Compound 1

1(a) Synthesis and Purification of Compound 1a 3-benzyloxycyclobutan-1-one is prepared according to the method described by McConathy et al (Appl Radiat Isotop 2003; 58: 657-666). 3-benzyloxycyclobutan-1-one is reacted with potassium cyanide, ammonium carbonate and ammonium chloride. 5-(3-benzyloxycyclobutane)hydantoin, is isolated by crystallization from the reaction mixture and ring-opened in refluxing Ba(OH)$_2$ (sat.). The reaction mixture is neutralized with H$_2$SO$_4$, precipitating BaSO$_4$ is filtered off and the amino acid is isolated by evaporation of the filtrate. 1-Amino-3-benzyloxy-cyclobutanecarboxylic acid is turned into 1-Amino-3-benzyloxy-cyclobutanecarboxylic acid ethyl ester by SOCl$_2$ and Et$_3$N in ethanol. Concentration of the reaction mixture in vacuum gives 1-Amino-3-benzyloxy-cyclobutanecarboxylic acid ethyl ester isolated as a salt mixture. The amino group is Boc-protected using boc anhydride in Et$_3$N and ethanol. 3-Benzyloxy-1-tert-butoxycarbonylamino-cyclobutanecarboxylic acid ethyl ester (Compound 1a) is isolated by extractive work-up, followed by flash chromatography.

1(b) Synthesis and Purification of Compound 1b

Compound 1a (prepared according to Example 1(a); 31.83 g, 91 mmol) was dissolved in ethanol (600 ml) and acetic acid (8 ml, 139 mmol) under an N$_2$ atmosphere in a reaction flask connected to an H$_2$-supply. The resulting mixture was added moistened Pd on carbon (6.28 g, 10% w/w). The N$_2$ supply was closed and the reaction flask was gently evacuated and filled with H$_2$, the procedure was repeated twice. Additional H$_2$ was added the reaction mixture when necessary. The reaction mixture was stirred at ambient temperature for 2 days, until complete conversion (reaction progress monitored by TLC). The reaction mixture was filtered through a glass fibre filter and the filter cake was washed with ethanol (160 ml) before the filtrate was evaporated in vacuo at <40° C. to afford crude Compound 1b (24.64 g). Crude Compound 1b was re-dissolved in dichloromethane (500 ml), added SiO$_2$ (65 g) and evaporated in vacuo at <40° C. to afford adsorbat for chromatographic purification.

System for flash chromatography: SiO$_2$ (360 g) was loaded into a glass column ø=13 cm to an approximate height of 5 cm and conditioned with heptane followed by heptane added 30% ethyl acetate. The crude compound was loaded on top of the column as adsorbat, sea sand (88 g) was carefully added on the top of the column. The column was then eluted with: heptane added 30% ethyl acetate (3 fractions in total 2000 ml), heptane added 50% ethyl acetate (8 fractions in total 2750 ml) and heptane added 70% ethyl acetate (8 fractions in total 4000 ml). The product was isolated in fractions 8-19, these fractions was combined and evaporated in vacuo at 38° C. to afford Compound 1b 20.1 g (86%). Purity GC 99.8%.

1(c) Synthesis and Purification of Compound 1

Compound 1b (20.1 g, 78 mmol) was dissolved in dichloromethane (500 ml) and added pyridine (19 ml, 235 mmol), resulting solution cooled to <5° C. and added triflic anhydride (19.5 ml, 115 mmol) in portions over 30 min. The reaction temperature was kept <5° C. during the addition, upon complete addition the reaction mixture was stirred on an ice-bath for 1 hr (reaction progress monitored by TLC), reaction quenched by addition of water (500 ml). The mixture was extracted with Et$_2$O (950 ml), water phase discarded, organic phase washed with HCl (500 ml, 1M), brine (500 ml, sat. aq.) and dried over Na$_2$SO$_4$ (56 g). The crude mixture was filtered through a glass sinter funnel, filter cake washed with Et$_2$O (100 ml), combined filtrate evaporated in vacuo at <30° C. to afford crude Compound 1 (28.11 g). Crude Compound 1 was re-dissolved in dichloromethane (400 ml), added SiO$_2$ (80 g) and evaporated in vacuo at <30° C. to afford adsorbat for chromatographic purification.

System for flash chromatography: SiO$_2$ (330 g) was loaded into a glass column 0=7 cm to an approximate height of 19 cm and conditioned with pentane:diethyl ether (3:1). The crude compound was loaded on top of the column as adsorbat, sea sand (50 g) was carefully added on the top of the column. The column was then eluted with pentane:diethyl ether (3:1), fraction size 250 ml, product was isolated in fractions 5-12 which was combined and evaporated in vacuo at <30° C. to afford Compound 121.94 g. To this material in an evaporator flask was added diethyl ether (50 ml) and slowly stirred on an evaporator at <35° C. until all solids had dissolved. Heating turned off and mixture slowly cooled to 25° C. over 1 h 5 min, solution stirred slowly for 1 h and 20 min at ambient temperature for 1 h 20 min. Subsequently the mixture was cooled to <5° C. and kept on this temperature for 20 min, before the mixture was further cooled to <−20° C. during 15 min and stirred at this temperature for 1 h 30 min. The solution was added heptane (110 ml) and stirred for 1 h 20 min. Crystals collected by filtration on a pre cooled glass sinter funnel, and washed with ice cold heptane (110 ml, <−5° C.). The reaction afforded Compound 119.47 g (64%), NMR purity +99%.

Example 2

Method of the Invention to Obtain Compound 1

0.5300 g of crude Compound 1b prepared according to the method described in Example 1(b) (i.e. including hydrogenation, filtration and evaporation but not flash chromatography) was dissolved in 5 ml absolute ethanol at ambient temperature. The solution was slowly concentrated up by blowing nitrogen. The crystals nucleated and grew during the procedure. After about one hour the evaporation was stopped. Amount of remaining ethanol was 0.3500 g (0.43 ml), and the mixture contained significant amount of crystals. 1 ml n-heptane was added and the evaporation by blowing continued. When the solvent mixture was almost evaporated (about 0.2 ml solvent left), the evaporation was stopped and 1 ml n-heptane added. After 15 min. the crystals were filtered off and washed with ~3 ml n-heptane. The crystals were dried in vacuum, the filtrate evaporated by blowing nitrogen and then dried in vacuum. The isolated yield was 0.4873 g crystals (91.9%), while recovery 92.9%:

|  | Amount g | Yield/ crude % | Yield/ recov. | Purity % | % syn-in Compound 1b |
|---|---|---|---|---|---|
| Crude | 0.5300 |  |  | 99.3 | 84.1 |
| Mother liq. | 0.0051 |  | 1.0 | 45.4 | 44.4 |
| Crystals | 0.4873 | 91.9 | 99.0 | 99.8 | 84.6 |
| Recovered | 0.4924 | 92.9 |  |  |  |

The crystals are well filterable, the size can be controlled by evaporation rate and also by addition rate of n-heptane.

Example 2

Method to Obtain Purified Compound 1b on a Lame Scale

Crude:
Crude reaction mixture from hydrogenation of Compound 1a to Compound 1b as ethanol solution after filtration of the catalyst and wash. Ethanol=2.5-3.8 liter.

Equipment:
Vacuum evaporator, evaporation flask, filtration equipment. The operation can be performed in a large evaporator flask initially, and transfer into a small flask after volume reduction. Alternatively, in a small flask of 500 or 1000 ml size, refilling the content continuously or in small portions.
1. The clear solution is concentrated by evaporation in vacuum flask down to a 100-200 ml total volume. The solution nucleates and the product crystallizes, forming a thick suspension.
2. 200 ml n-hexane is added and after 10 min stirring (rolling), the suspension is concentrating up to about 150 ml volume.
3. A new portion of 200 ml n-heptane is added and Step 2 is repeated.
4. After 30 min. rolling (ambient temperature or bellow) the suspension is filtered and the crystals washed by n-heptane.
5. The crystals are dried in vacuum.

The invention claimed is:
1. A method to obtain a compound of Formula I:

(I)

wherein:
$R^1$ represents a $C_{1-5}$ straight- or branched-chain alkyl group;
$R^2$ represents an amino protecting group;
v is an integer of 0 to 4; and,
X represents a leaving group selected from a halogen, or the group —O—SO$_2$—R$^3$ wherein R$^3$ is a halogen, a straight-chain or branched-chain $C_{1-10}$ alkyl, a straight-chain or branched-chain $C_{1-10}$ haloalkyl, and a $C_{6-10}$ aryl wherein said method comprises:
(a) debenzylation of a compound of Formula Ia:

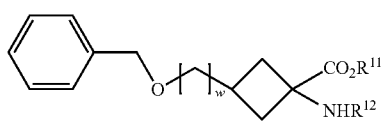
(Ia)

wherein $R^{11}$, $R^{12}$ and w are as defined for $R^1$, $R^2$ and v of Formula I, respectively;

(b) crystallisation of the reaction mixture from step (a) to obtain purified compound of Formula Ib:

(Ib)

wherein $R^{21}$, $R^{22}$ and x are as defined for $R^1$, $R^2$ and v of Formula I, respectively
(c) conversion of purified compound of Formula I obtained in step (b) into a compound of Formula I by reaction with a suitable form of X wherein X is as defined for Formula I.

2. The method as defined in claim 1 wherein $R^1$, $R^{11}$ and $R^{21}$ are ethyl.

3. The method as defined in claim 1 wherein $R^2$, $R^{12}$ and $R^{22}$ are selected from the group consisting of a t-butoxycarbonyl group, an allyloxycarbonyl group, a phthalimide group and N-benzylideneamine substituent.

4. The method as defined in claim 1 wherein v, w and x are 0 or 1.

5. The method as defined in claim 1 wherein X is a group represented by the group —O—SO$_2$—R$^3$.

6. The method as defined in claim 5 wherein R$^3$ is selected from the group consisting of toluenesulfonic acid, nitrobenzenesulfonic acid, benzenesulfonic acid, trifluoromethanesulfonic acid, fluorosulfonic acid, perfluoroalkylsulfonic acid, trimethylstannyl and triethylstannyl.

7. The method as defined in claim 6 wherein R$^3$ is trifluoromethanesulfonic acid.

8. The method as defined in claim 1 wherein said compound of Formula I is:

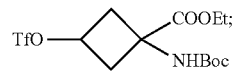

said compound of Formula Ib is:

and,
and said compound of Formula Ia is:

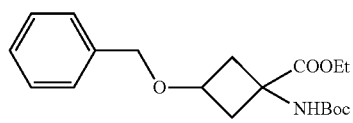

wherein Et is ethyl, OTf is trifluoromethanesulfonic acid and Boc is tert-Butyloxycarbonyl.

9. The method as defined in claim 1 wherein X is halogen.

10. The method as defined in claim 1 wherein said halogen is bromo or chloro.

11. A radiosynthetic method to obtain a compound of Formula II:

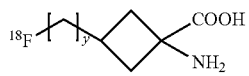 (II)

wherein y is as defined for v in claim 1, wherein said method comprises;
(i) providing a compound of Formula I according to the method as defined in claim 1;
(ii) reaction of said compound of Formula I with a suitable source of $^{18}F$-fluoride to obtain a compound of Formula IIa:

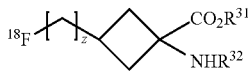 (IIa)

wherein $R^{31}$, $R^{32}$ and z are as defined in claim 1 for $R^1$, $R^2$ and v, respectively; and,
(iii) deprotection of the compound of Formula IIa obtained in step (ii) to remove $R^{31}$ and $R^{32}$.

12. The method as defined in claim 11 wherein said source of $^{18}F$-fluoride is $^{18}F$-fluoride in the presence of a counterion wherein said counterion is selected from, rubidium, caesium, potassium complexed with a cryptand, or a tetraalkylammonium salt.

13. The method as defined in claim 11 wherein said deprotection comprises removal of $R^{31}$ followed by removal of $R^{32}$.

14. The method as defined in claim 11 wherein y and z are the same and are 0 or 1.

15. The method as defined in claim 11 wherein $R^{31}$ is ethyl.

16. The method as defined in claim 11 wherein $R^{32}$ is a t-butoxycarbonyl group.

17. The method as defined in claim 11 wherein said compound of Formula II is:

and said compound of Formula IIa is:

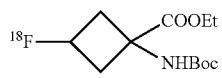

wherein Et is ethyl and Boc is tert-Butyloxycarbonyl.

18. The method as defined in claim 17 wherein said deprotection step comprises removal of Et by basic hydrolysis and removal of Boc by acidic hydrolysis.

19. The method as defined in claim 11 wherein steps (ii) and (iii) are carried out on an automated synthesiser.

* * * * *